(12) United States Patent
Malandain

(10) Patent No.: US 7,524,323 B2
(45) Date of Patent: Apr. 28, 2009

(54) SUBCUTANEOUS SUPPORT

(75) Inventor: Hugues F. Malandain, Mountain View, CA (US)

(73) Assignee: Kyphon SARL (CH)

( * ) Notice: Subject to any disclaimer, the term of this patent is extended or adjusted under 35 U.S.C. 154(b) by 484 days.

(21) Appl. No.: 10/826,684

(22) Filed: Apr. 16, 2004

(65) Prior Publication Data
US 2005/0234452 A1   Oct. 20, 2005

(51) Int. Cl.
*A61B 17/70* (2006.01)
(52) U.S. Cl. ...................................................... 606/246
(58) Field of Classification Search ................. 606/54, 606/60, 61, 69–72, 246, 250–253, 264–275, 606/280–296
See application file for complete search history.

(56) References Cited

U.S. PATENT DOCUMENTS

| | | | |
|---|---|---|---|
| 3,779,240 A | 12/1973 | Kondo | |
| 4,493,317 A | 1/1985 | Klaue | |
| 4,763,644 A | 8/1988 | Webb | |
| 4,805,602 A | 2/1989 | Puno et al. | |
| 4,946,458 A | 8/1990 | Harms et al. | |
| 5,005,562 A | 4/1991 | Cotrel | |
| 5,053,036 A | 10/1991 | Perren et al. | |
| 5,057,111 A | 10/1991 | Park | |
| 5,129,388 A | 7/1992 | Vignaud et al. | |
| 5,129,899 A * | 7/1992 | Small et al. | 606/61 |
| 5,147,361 A | 9/1992 | Ojima et al. | |
| 5,151,103 A | 9/1992 | Tepic et al. | |
| 5,171,279 A | 12/1992 | Mathews | |
| 5,176,678 A | 1/1993 | Tsou | |
| 5,176,679 A | 1/1993 | Lin | |
| 5,180,381 A | 1/1993 | Aust et al. | |
| 5,207,678 A | 5/1993 | Harms et al. | |
| 5,234,431 A | 8/1993 | Keller | |
| 5,246,442 A | 9/1993 | Ashman et al. | |
| 5,253,406 A | 10/1993 | Shere et al. | |
| 5,261,909 A | 11/1993 | Sutterlin et al. | |
| 5,269,784 A | 12/1993 | Mast | |
| 5,290,288 A * | 3/1994 | Vignaud et al. | 606/61 |
| 5,324,290 A | 6/1994 | Zdeblick et al. | |
| 5,360,431 A | 11/1994 | Puno et al. | |
| 5,395,371 A | 3/1995 | Miller et al. | |
| 5,429,639 A | 7/1995 | Judet | |
| 5,443,467 A | 8/1995 | Biedermann et al. | |

(Continued)

FOREIGN PATENT DOCUMENTS

DE        94 02 695 U1    4/1994

(Continued)

*Primary Examiner*—Eduardo C Robert
*Assistant Examiner*—Michael J Araj
(74) *Attorney, Agent, or Firm*—Krieg Devault LLP

(57) ABSTRACT

An implantable medical device and methods of use thereof are provided for supporting a structure. The structure supported can include a bony structure. The device is comprised of a support element having a top portion, a bottom portion having a bottom surface and one or more apertures passing therethrough. The bottom surface of the support element includes a receiver configured to receive a plurality of anchor assemblies. Each of the anchor assemblies includes a means for locking the anchor assembly to the support element, and a base having a head and a means for locking the base to the anchor assembly. When assembled, the head of the base for the anchor assembly may not pass through the support element.

38 Claims, 7 Drawing Sheets

U.S. PATENT DOCUMENTS

| | | | |
|---|---|---|---|
| 5,466,237 A | 11/1995 | Byrd, III et al. | |
| 5,474,551 A | 12/1995 | Finn et al. | |
| 5,474,555 A | 12/1995 | Puno et al. | |
| 5,476,464 A | 12/1995 | Metz-Stavenhagen et al. | |
| 5,480,401 A | 1/1996 | Navas | |
| 5,480,440 A | 1/1996 | Kambin | |
| 5,499,983 A | 3/1996 | Hughes | |
| 5,501,684 A | 3/1996 | Schlapfer et al. | |
| 5,520,690 A | 5/1996 | Errico et al. | |
| 5,531,746 A | 7/1996 | Errico et al. | |
| 5,549,608 A | 8/1996 | Errico et al. | |
| 5,554,157 A | 9/1996 | Errico et al. | |
| 5,575,792 A | 11/1996 | Errico et al. | |
| 5,578,033 A | 11/1996 | Errico et al. | |
| 5,584,834 A | 12/1996 | Errico et al. | |
| 5,586,984 A | 12/1996 | Errico et al. | |
| 5,591,166 A * | 1/1997 | Bernhardt et al. | 606/61 |
| 5,607,426 A | 3/1997 | Ralph et al. | |
| 5,609,593 A | 3/1997 | Errico et al. | |
| 5,647,873 A | 7/1997 | Errico et al. | |
| 5,649,926 A | 7/1997 | Howland et al. | |
| 5,669,911 A | 9/1997 | Errico et al. | |
| 5,672,176 A | 9/1997 | Biedermann et al. | |
| 5,733,285 A | 3/1998 | Errico et al. | |
| 5,733,286 A | 3/1998 | Errico et al. | |
| 5,817,094 A | 10/1998 | Errico et al. | |
| 5,876,403 A | 3/1999 | Shitoto et al. | |
| 5,882,350 A | 3/1999 | Ralph et al. | |
| 5,885,286 A | 3/1999 | Sherman et al. | |
| 5,951,553 A | 9/1999 | Betz et al. | |
| 5,964,761 A * | 10/1999 | Kambin | 606/61 |
| 5,964,988 A | 10/1999 | LaRose et al. | |
| 6,022,350 A | 2/2000 | Ganem | |
| 6,030,389 A | 2/2000 | Wagner et al. | |
| 6,053,917 A | 4/2000 | Sherman et al. | |
| 6,063,090 A | 5/2000 | Schlapfer | |
| 6,074,391 A | 6/2000 | Metz-Stavenhagen et al. | |
| 6,077,262 A | 6/2000 | Schlapfer et al. | |
| 6,090,110 A | 7/2000 | Metz-Stavenhagen | |
| 6,090,111 A | 7/2000 | Nichols | |
| 6,113,601 A | 9/2000 | Tatar | |
| 6,280,442 B1 | 8/2001 | Barker et al. | |
| 6,296,644 B1 | 10/2001 | Saurat et al. | |
| 6,315,779 B1 * | 11/2001 | Morrison et al. | 606/69 |
| 6,585,738 B1 | 7/2003 | Mangione et al. | |
| 6,682,530 B2 * | 1/2004 | Dixon et al. | 606/61 |
| 6,736,817 B2 | 5/2004 | Troxell et al. | |
| 6,755,829 B1 | 6/2004 | Bono et al. | |
| 6,858,031 B2 * | 2/2005 | Morrison et al. | 606/69 |
| 6,884,241 B2 * | 4/2005 | Bertranou et al. | 606/61 |
| 6,887,241 B1 | 5/2005 | McBride et al. | |
| 7,220,262 B1 | 5/2007 | Hynes | |
| 2002/0007183 A1 | 1/2002 | Lee et al. | |
| 2002/0026194 A1 | 2/2002 | Morrison et al. | |
| 2003/0032957 A1 | 2/2003 | McKinley et al. | |
| 2003/0105460 A1 | 6/2003 | Crandall et al. | |
| 2003/0114853 A1 | 6/2003 | Burgess et al. | |
| 2003/0135210 A1 | 7/2003 | Dixon et al. | |
| 2004/0087949 A1 | 5/2004 | Bono et al. | |
| 2004/0092931 A1 | 5/2004 | Taylor et al. | |
| 2004/0127897 A1 | 7/2004 | Freid et al. | |
| 2004/0225290 A1 | 11/2004 | Ferree | |
| 2005/0038434 A1 | 2/2005 | Mathews | |
| 2005/0049588 A1 | 3/2005 | Jackson | |
| 2005/0049593 A1 * | 3/2005 | Duong et al. | 606/69 |
| 2005/0113927 A1 | 5/2005 | Malek | |
| 2005/0215999 A1 | 9/2005 | Birkmeyer et al. | |
| 2005/0234451 A1 | 10/2005 | Markworth | |
| 2005/0234456 A1 * | 10/2005 | Malandain | 606/69 |
| 2006/0149237 A1 | 7/2006 | Markworth et al. | |
| 2006/0149252 A1 | 7/2006 | Markworth et al. | |

FOREIGN PATENT DOCUMENTS

| | | |
|---|---|---|
| FR | 2 780 631 | 1/2000 |
| WO | 2000/054681 | 9/2000 |
| WO | 02/76315 | 10/2002 |
| WO | 2004/064603 | 8/2004 |
| WO | 2004/093701 | 11/2004 |

* cited by examiner

SUBCUTANEOUS SUPPORT

TECHNICAL FIELD

This invention relates to medical devices.

BACKGROUND

The use of spinal stabilization/fixation devices to align or position specific vertebrae or a region of the spine is well established. Typically such devices utilize a spinal fixation element, comprised of a relatively rigid member such as a plate, board or rod that is used as a coupler between adjacent vertebrae. Such a spinal fixation element can effect a rigid positioning of adjacent vertebrae when attached to the pedicle portion of the vertebrae using pedicle bone anchorage screws. Once the coupled vertebrae are spatially fixed in position, procedures can be performed, healing can proceed or spinal fusion may take place.

Spinal fixation elements may be introduced posteriorly to stabilize the various vertebrae of the spine for example in conjunction with a kyphoplasty procedure wherein a void or cavity is made inside a vertebral body followed by filling with a bone substitute to form an "internal cast." Some devices for this purpose are designed to be attached directly to the posterior of the spine, but the generally invasive nature of a conventional paraspinal approach used to implant these devices poses drawbacks. One minimally invasive solution to the problem of the paraspinal approach involves making a longitudinal separation between the sacrospinalis group of muscles rather than between the lateral border of the sacrospinalis group and quadratus lumborum. Problems stemming from the prior art solutions include a high degree of invasiveness resulting in muscle disruption and blood loss. Additionally, the prior art solutions are time consuming and are difficult to remove.

SUMMARY

In general, in one aspect, the invention provides an implantable medical device for supporting a structure comprising a support element having a top portion, a bottom portion having a bottom surface and one or more apertures passing therethrough. The bottom portion of the support element includes a receiver for a plurality of anchor assemblies. Each anchor assembly includes a means for locking the anchor assembly to the support element, a base having a head and a means for locking the base to the anchor assembly. When the support element and the anchor assembly are assembled, the base does not pass through the support element.

Aspects of the invention provide numerous advantages.

The structure supported by the device can be a bony structure. Alternatively, the structure supported can be the spine. In one implementation, the posterior of the spine can be the supported structure. In other implementations, other portions of the spine are the supported structure. In yet other implementations, the structure supported can include a femur or other bones of the leg (e.g. tibia and fibula), bones of the arm and wrist (e.g. humerus, radius and ulna), calcaneous, pelvis, spine and the like.

The base of the anchor assembly of the device can be comprised of a base head that is movably disposed within the anchor assembly.

The support element can have one or more apertures with a dimensional configuration providing access to the base, as well as the means for locking the base to the anchor assembly, through the top portion of the support element. The support element apertures are configured such that the head of the base disposed within the anchor assembly does not pass through the support element. In one implementation, the support element of the device is elongated and can have a shape selected from the group consisting of a board, plate, elongated cross-section, oval, square, I-beam and a rod. Additionally, the support element can be sized to substantially span two or more vertebrae of the spine. The support element can be comprised of a material selected from the group consisting of titanium, stainless steel, carbon fiber, a biocompatible material, a reabsorbable material and composites thereof.

The receiver can be integrally disposed within the bottom surface of the bottom portion of the support element. In one implementation, the receiver can be attached to the bottom surface of the bottom portion of the support element. In another implementation, the receiver can have a configuration selected from the group consisting of a slot, groove, track, dovetail and one-way snap-in configuration. Additionally, the receiver can have a 90-degree twist-in configuration. Alternatively, the receiver and the anchor assembly can interconnect through a T-slot configuration. In the T-slot implementation, the receiver can include a planar upper face, a planar lower face and a planar medial face.

The receiver can substantially span the length of the bottom surface of the bottom portion of the support element, and have a plurality of ends. The receiver can have a first end that is open and a second end that is closed. Additionally, the receiver can have first and second ends that are both open. Alternatively, the receiver can have first and second ends that are both closed. The receiver can have a plurality of access ports sized for coupling the anchor assembly to the receiver distally from the receiver ends. Additionally, the receiver can be configured to receive the anchor assemblies in two dimensions.

The anchor assembly can be of a configuration selected from the group consisting of a slot, groove, track, dovetail and one-way snap-in configuration. It can have a 90-degree twist-in configuration or a T-slot configuration. The anchor assembly can be comprised of a material selected from the group consisting of titanium, stainless steel, carbon fiber, a biocompatible material, a reabsorbable material and composites thereof.

The means for locking the anchor assembly to the support element can be comprised of a setscrew disposed within a threaded anchor assembly locker aperture. The setscrew can be threaded so as to lockably engage the receiver planar upper face upon turning, such that upon so engaging the receiver planar upper face, the setscrew causes the anchor assembly to press against the receiver lower planar face to effect locking. Alternatively, the means for locking the anchor assembly to the support element can be a cam. The means for locking the anchor assembly to the support element can be comprised of a threaded blind aperture having a tapered slot substantially aligned longitudinally with the receiver thereby providing expandable walls, a floor having a channel cut through therethrough and a setscrew. Turning the setscrew into the blind aperture causes the walls to expand outwardly to engage the receiver planar medial surface to effect locking. Alternatively, the blind aperture is configured for a cam to effect locking of the anchor assembly to the support element in a manner analogous that described for a setscrew.

The base of the anchor assembly can be selected from the group consisting of a screw, staple, nail, hook and a pin. The screw can be a bone anchorage screw. The bone anchorage screw can be a pedicle screw. The base head of the anchor assembly base can be polyaxial or a hinge-type connector. The base can have a means for locking the base in a desired position. The means for locking the base in position can be comprised of a threaded base aperture and a setscrew; wherein turning the setscrew into the threaded base aperture results in engagement of the base head to effect locking. Alternatively, the means for locking the base is a cam wherein the cam is disposed such that turning the cam results in engagement of the base head with the cam to effect locking.

A method for supporting a spine using the device can include the steps of: implanting a plurality of anchor assemblies having bases into the pedicles of adjacent vertebrae of a spine; connectively positioning a support element having a receiver for the anchor assemblies on top of the anchor assemblies; locking the bases within the anchor assemblies; and locking the anchor assemblies within the support element receiver. In one implementation, the support element can be disposed within a body location selected from the group consisting of the subcutaneous fat layer of the back, muscle, cartilage and a bone. In another implementation, the support element is disposed adjacent to bone. In yet another implementation, the support element is disposed adjacent to the spine. In another implementation, the support element is disposed external to the body.

A method of use of the invention for effecting a desired vertebral disk spacing, can include the steps of: 1) implanting the bases of a plurality of anchor assemblies into vertebrae, wherein the bases of the anchor assemblies are unlocked for free movement; 2) interconnecting the anchor assemblies with the receiver of the support element 1, wherein the anchor assemblies are unlocked within the receiver; 3) locking the bases within the anchor assemblies using a setscrew or cam; 4) compressing or distracting the bases in relation to each other to achieve a parallel displacement of the instrumented vertebrae; and 5) locking the anchor assemblies within the support element using a set screw or cam.

A method of use of the invention for effecting a desired curvature of the spine can include the steps of: 1) implanting the bases of a plurality of anchor assemblies into vertebrae, wherein the bases of the anchor assemblies are unlocked for free movement; 2) interconnecting the anchor assemblies with the receiver of the support element, wherein the anchor assemblies are unlocked within the receiver; 3) compressing or distracting the bases in relation to each other to affect the lordotic/kyphotic curvature of the spine; 4) locking the bases within the anchor assemblies and locking the anchor assemblies within the support element, using a setscrew or cam.

Another method of using the invention to support the spine can include the steps of: 1) setting a series of anchor assemblies percutaneously in place along the spine through a series of small incisions including screwing a bone anchorage screw of each anchor assembly into one or more adjacent pedicle portions of adjacent vertebrae in the spine, such that the anchor assemblies' receiver mating parts align in a parallel plane within the subcutaneous fat layer of the back; 2) loading the support element on top of the anchor assemblies including engaging the mated parts of the receiver and the anchor assembly, either by sliding, snapping or otherwise positioning the support element into the desired position; 3) accessing and locking the anchor assembly in the support element using the locking means feature of the anchor assembly via the support element apertures; and 4) optionally locking the bone anchorage screw feature of the anchor assembly using the locking means feature for the bone anchorage screw via the support element apertures.

A minimally invasive, low profile implant device for supporting the spine is provided. The present invention provides an implantable medical device and methods useful for supporting a body structure, such as the spine, using a percutaneously disposed support element combined with a plurality of anchor assemblies having movably attached bases. Each base can be a bone anchorage screw. Alternatively, each base is a bone staple, nail, hook or screw. The assembled support element and anchor assembly provide support to the spine without the need for passage of a bone anchorage screw through the support element. The base features of the anchor assemblies can be of a type used for insertion into the pedicles of vertebrae. The support element is configured for mated placement on top of a number of anchor assemblies and can be locked in place. Locking of the anchor assemblies within the support element is effected through the top of the support element via apertures passing through the support element. The bone anchorage screw feature can optionally be locked to prevent movement within the anchor assembly to further support the spine.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

As shown in FIG. 1 and FIGS. 2A-D, a support element 1 is provided having a shape. The support element 1 preferably is elongate and of a sufficient length to span a number of vertebrae in the spine. The support element 1 shape can include board, elongated cross-section, rod, oval, square, and I-beam. The length of the support element 1 is minimally substantially the same length as required to span two or more vertebrae. Preferably, the support element 1 is substantially the same length as required to span three vertebrae. In one implementation, the length of the support element 1 is substantially between 25 to 140 millimeters. The support element 1 can be made of materials that are durable and that can be implanted in a body, including titanium, stainless steel, carbon fiber, etc. In one implementation, the support element 1 is made of titanium. In another implementation the support element 1 is made of a biocompatible material. Additionally, the support element 1 can be made of a reabsorbable material. Furthermore, the support element can be made of a composite of any of the forgoing materials. In use, the support element 1 and attending anchor assemblies (described in detail below) can be used for temporary or permanent implantation.

Figure 1:
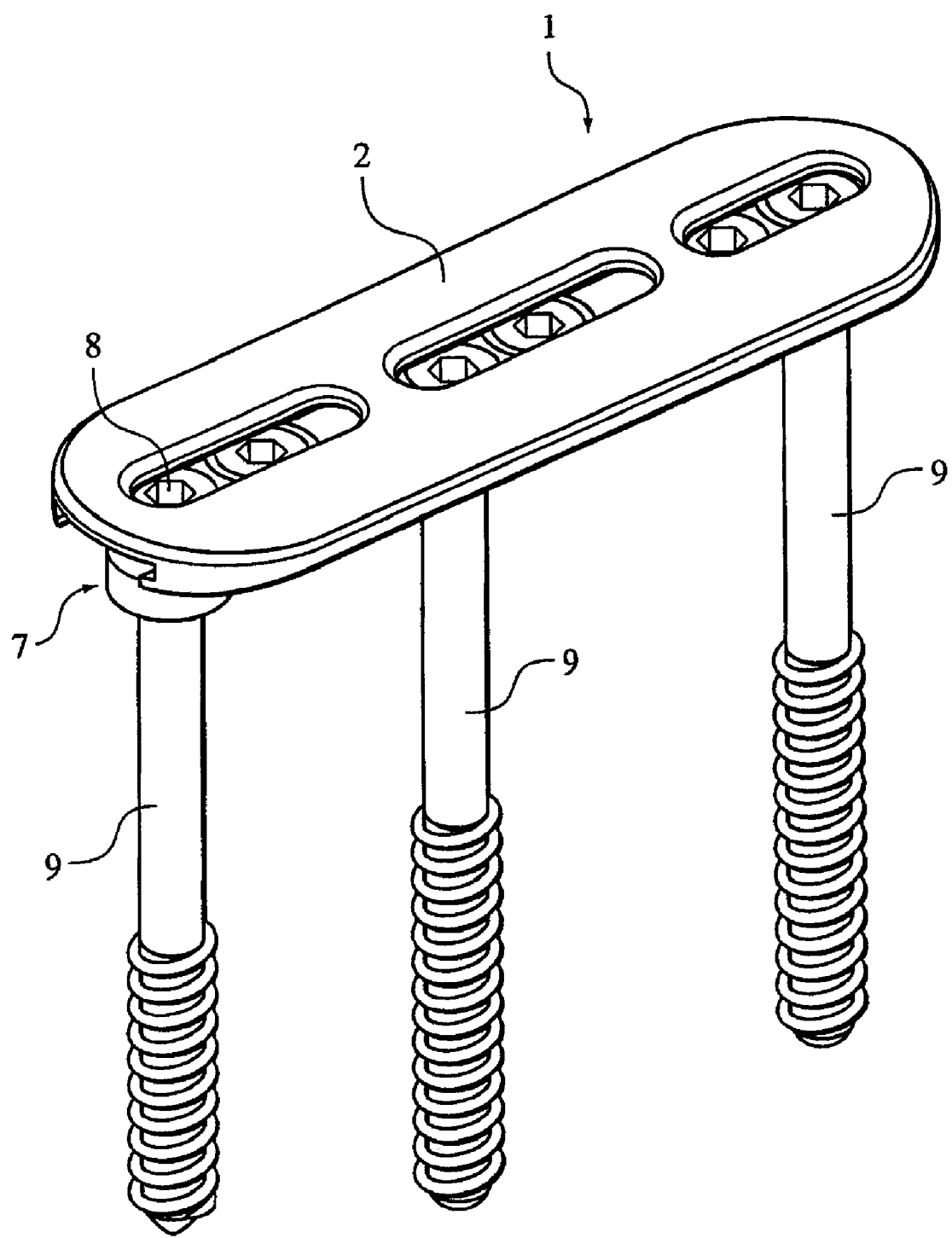
FIG. 1 is a drawing of the device showing three anchor assemblies positioned within the support element.
Figure 2A:
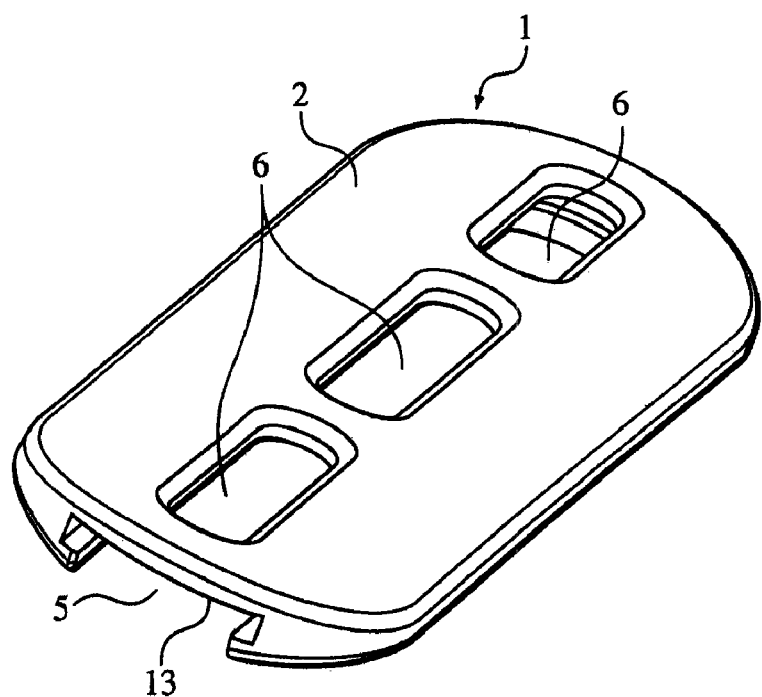
FIG. 2A is a drawing showing a top view of the support element, illustrating the receiver and apertures.
Figure 2B:
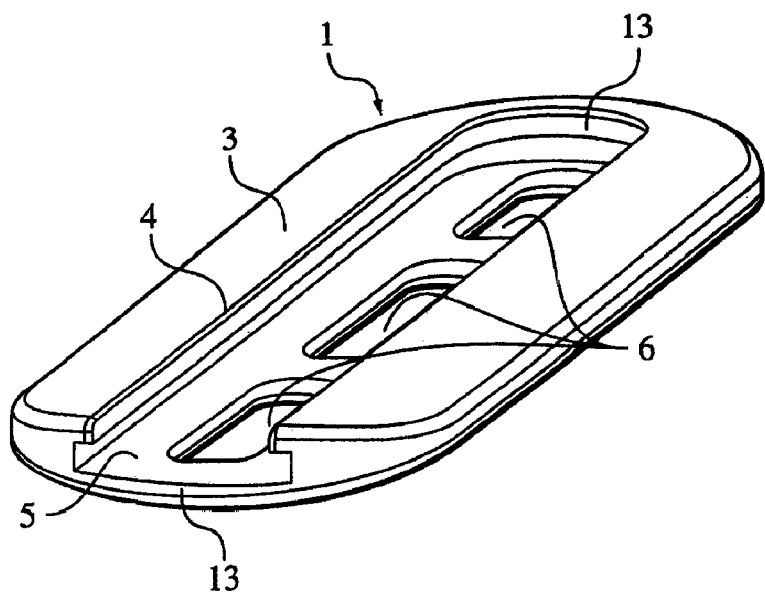
FIG. 2B is a drawing showing a bottom view of the support element, illustrating the receiver and apertures.

As shown in FIGS. 2A-D, the support element 1 includes a top portion 2 and a bottom portion 3 having a bottom surface 4 and a receiver 5. Additionally, as shown in FIGS. 2A and 2B, the support element 1 can include a number of centrally aligned apertures 6. The apertures 6 can have any of a number of shapes not limited to openings having a round, oval or elongate shape. Any number of apertures 6 can be employed, including one or more. In one implementation, three apertures 6 per support element 1 are included (See FIGS. 1, 2A, 2B and 2D). Any type of spacing of apertures 6 can be used, including even or staggered. In one implementation, the apertures 6 are spaced evenly and separated by a distance substantially equivalent to the spacing of the vertebrae of a spine. Alternatively, the apertures 6 can be spaced closer together than the spacing of vertebrae of a spine. The aperture(s) 6 are sized for and limited to a size sufficient for accessing the features of the anchor assembly 7 (described in detail below) with a tool or object through the top portion 2 of the support element 1 (e.g. to engage the locking means of the anchor assembly 7 using, for example, a hex-headed screw driver). In this way, as shown in FIG. 1, when the support element 1 and the anchor assembly 7 are assembled, the base head 8 of the base 9 (both described in detail below), though accessible through the support element 1, does not pass through the support element 1. In use (i.e., assembled with a plurality of anchor assemblies) the support element 1 top portion 2 can have a smooth surface with no protruding features (e.g., screw heads or the like).

In another implementation, the aperture(s) 6 are sized such that when the support element 1 and the anchor assembly 7 are assembled, the base head 8 portion of the base 9 can pass through the support element 1 (e.g., from beneath), but the base 9 does not pass through the support element 1 (not shown). In yet another implementation, the aperture(s) 6 are sized such that the base 9 can pass completely through the support element 1 (not shown).

Figure 2C:
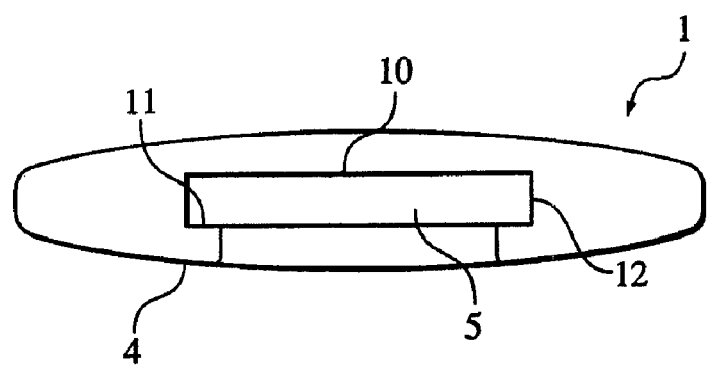
FIG. 2C is a drawing showing an end view of the support element, illustrating the receiver.
Figure 2D:
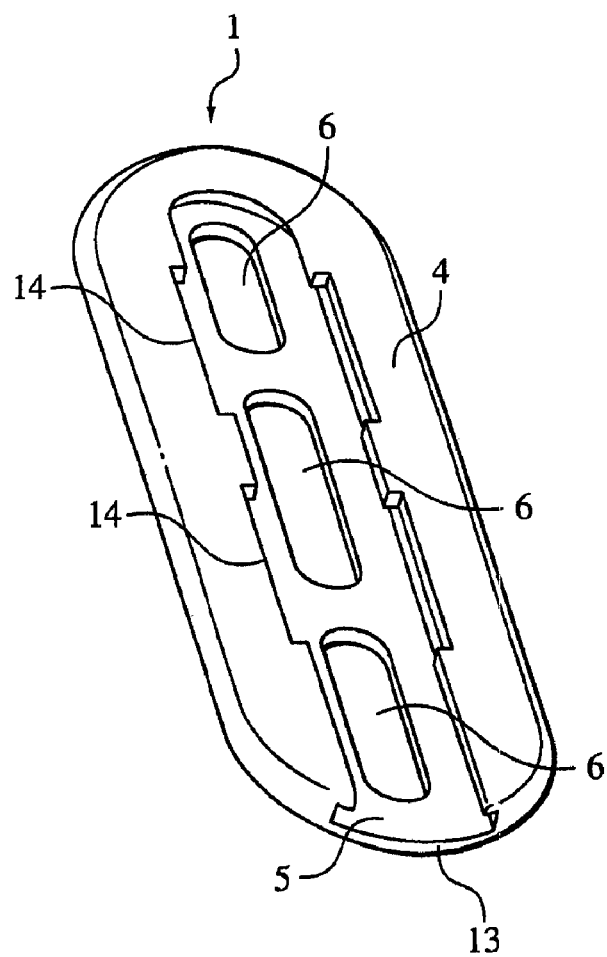
FIG. 2D is a drawing showing two bottom views of the support element, illustrating the anchor assembly access ports.
Figure 2D:
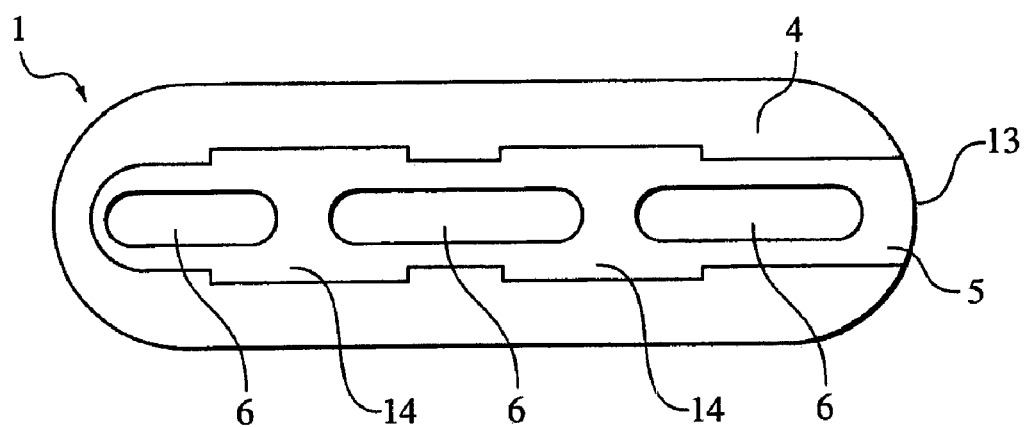

As shown in FIGS. 2A-D the support element 1 includes a receiver 5 that is integrally disposed within the bottom surface 4 of the support element 1. Alternatively, the receiver 5 can be coupled to the bottom surface 4 of the support element 1 (for example a track-type receiver 5 can be attached by rivets or screws to the bottom surface 4 of the support element 1). The receiver 5 can be configured as a slot, groove, track, dovetail, one-way snap-in design, or the like. In one implementation, the receiver 5 is configured in a 90-degree twist-in configuration, wherein the base head 8 of the anchor assembly 7 base 9 has two dimensions. The first dimension allows the base head 8 to pass into the receiver 5. As the base head 8 is rotated 90 degrees with respect to the receiver 5 and, upon completing the 90-degree rotation, the second dimension maintains the base 9 in the receiver 5. In another implementation, as shown in FIGS. 2A-C, the receiver 5 is a T-slot configuration. As shown in FIG. 2C, the receiver 5 includes a planar upper face 10, a planar lower face 11 and a planar medial face 12. Alternatively, where the configuration of the receiver 5 is dovetail, the receiver 5 includes a planar upper face 10 and an angled face. In yet another alternative, where the receiver 5 is of a curved or rounded shape, the receiver 5 includes a curved or rounded receiver 5 face. The receiver 5 can span all or part of the length of the bottom surface 4 of the support element 1. As shown in FIGS. 2A, 2B and 2D, each end 13 of the receiver 5 can be open or closed. In one implementation, both ends 13 of the receiver 5 are open (not shown). In another implementation, one end 13 of the receiver 5 is open and the opposite end 13 is closed (see FIGS. 2B and 2D). In another implementation, both ends 13 of the receiver 5 are closed (not shown).

As shown in FIG. 2D, the receiver 5 can include anchor assembly access ports 14 that provide openings in the pathway of the receiver 5, whereby the anchor assemblies 7 can be interconnected to the support element 1 without having to traverse the length of the receiver 5 when accommodating multiple (or even a single) anchor assemblies 7. The anchor assembly access ports 14 can be of a sufficient size to accept the anchor assembly 7 and can be spaced evenly, or staggered as desired.

Figure 3C:
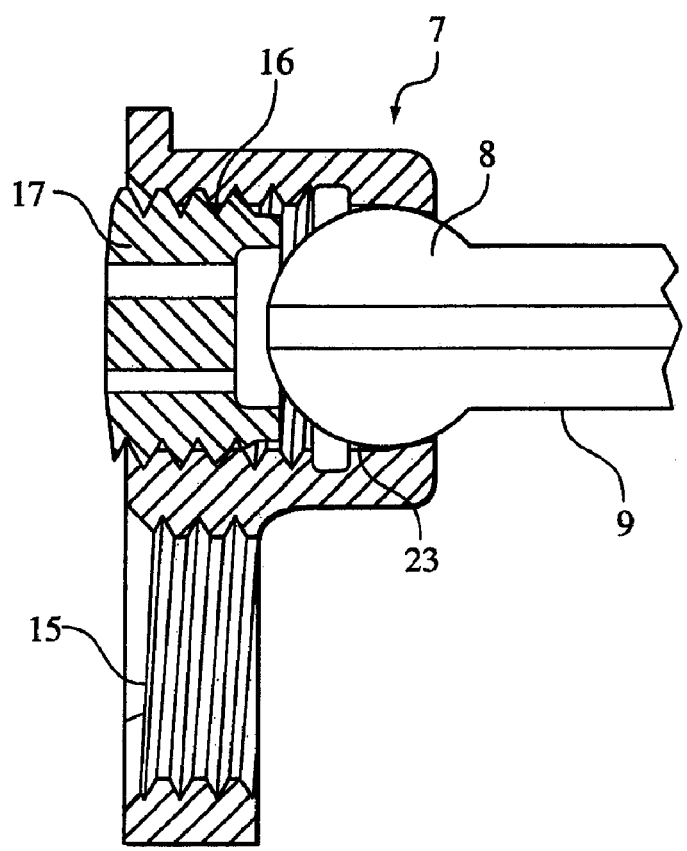
FIG. 3C is a drawing showing a cutaway view of the anchor assembly, illustrating the base head, the receptacle, the base aperture and the setscrew.
Figure 3A:
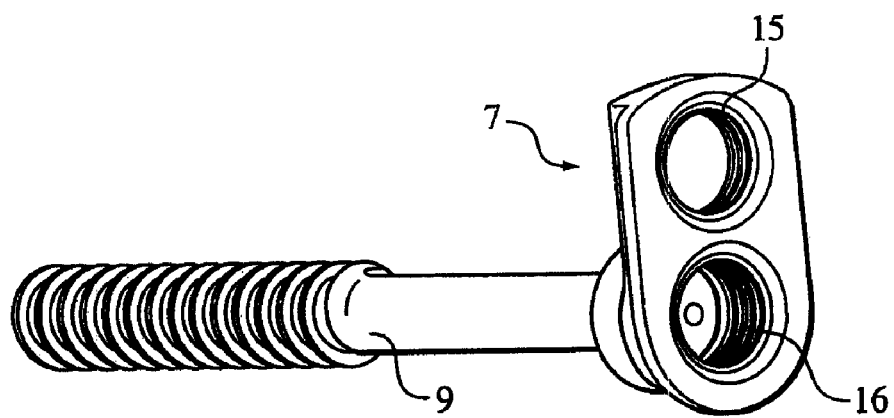
FIG. 3A is a drawing showing a side view of the anchor assembly, illustrating the base, the locker aperture and the base aperture.
Figure 3B:
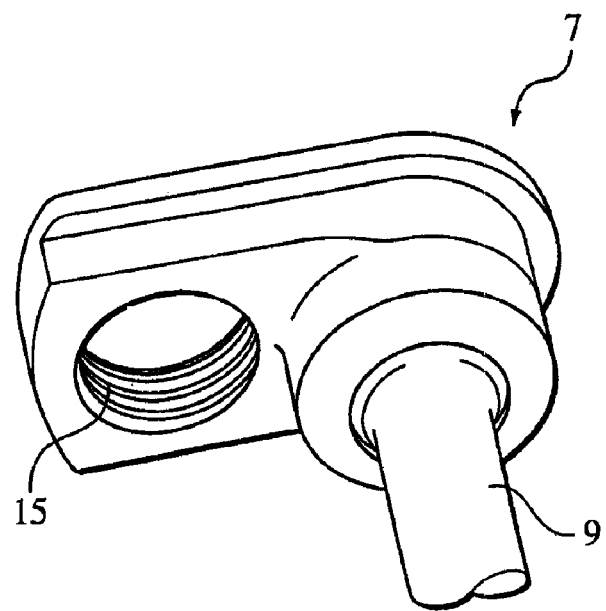
FIG. 3B is a drawing showing a bottom view of the anchor assembly, illustrating the base and the threaded anchor assembly locker aperture.

As shown in FIGS. 2A-C, 3A, 3B and 4A, the anchor assembly 7 is configured to interconnect with the shape of the receiver 5. As described above for the receiver 5, the anchor assembly 7 complimentary shapes can be any of a number of shapes. In some implementations, the mating between the support element 1 and the anchor assembly 7 occurs only in two dimensions (e.g. where a 90 degree twisting receiver 5 is employed). As shown in FIGS. 3A and 3B, the anchor assembly 7 can be comprised of a threaded anchor assembly 7 locker aperture 15 and a threaded base aperture 16. The anchor assembly 7 can be comprised of numerous materials that are durable and that can be implanted in a body, including titanium, stainless steel, carbon fiber, etc. Additionally, the anchor assembly 7 can be comprised of a reabsorbable material or a biocompatible material. Furthermore, the anchor assembly can be made of a composite of any of the forgoing materials.

Figure 4A:
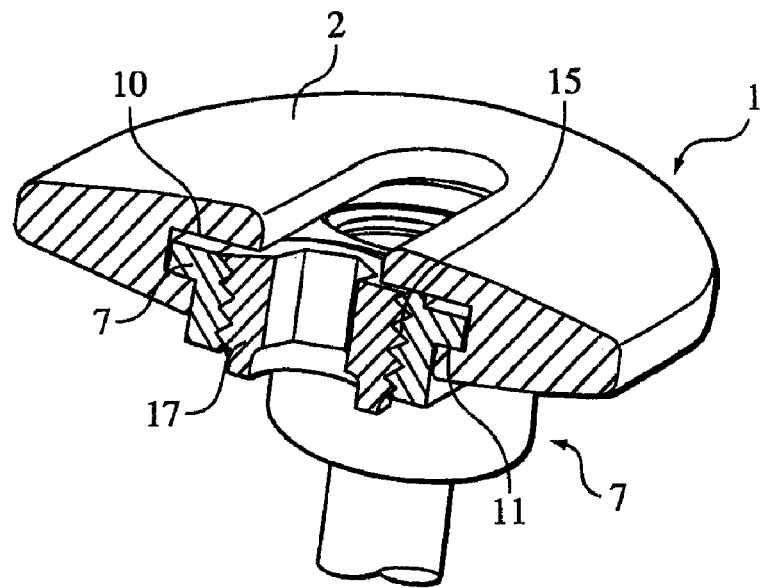
FIG. 4A is a drawing showing the locker aperture and setscrew means for locking the anchor assembly to the support element.
Figure 4B:
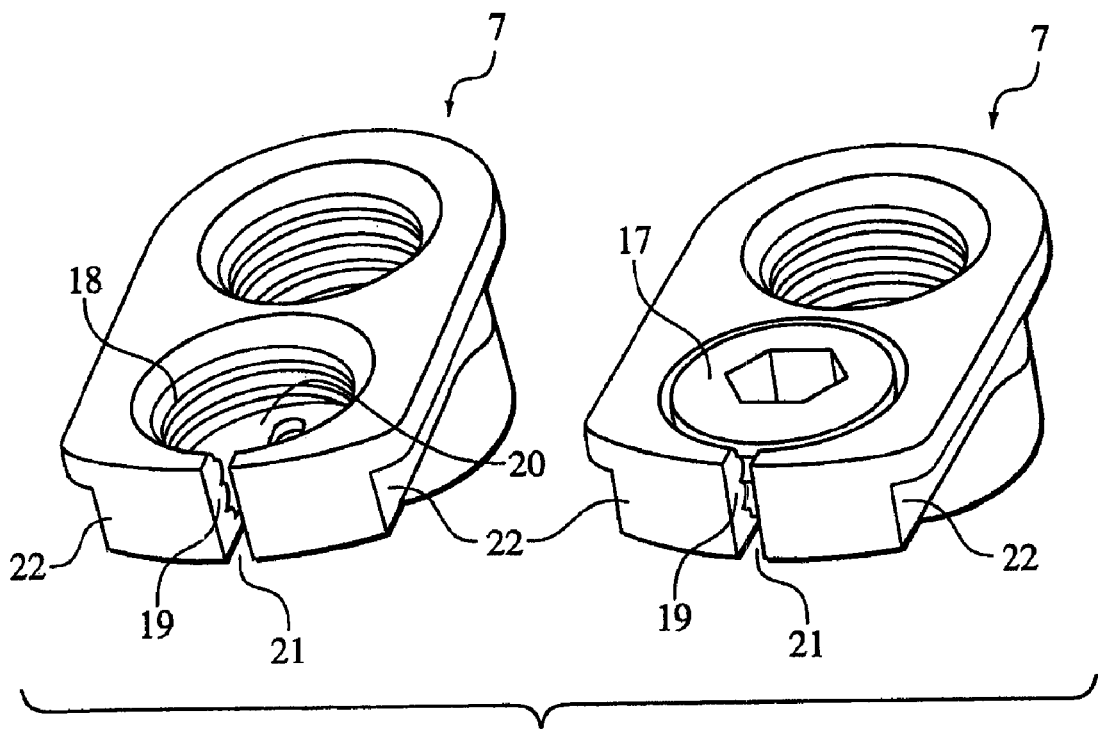
FIG. 4B is a drawing showing two views of a threaded blind aperture with slot and setscrew means for locking the anchor assembly to the support element.
Figure 4C:
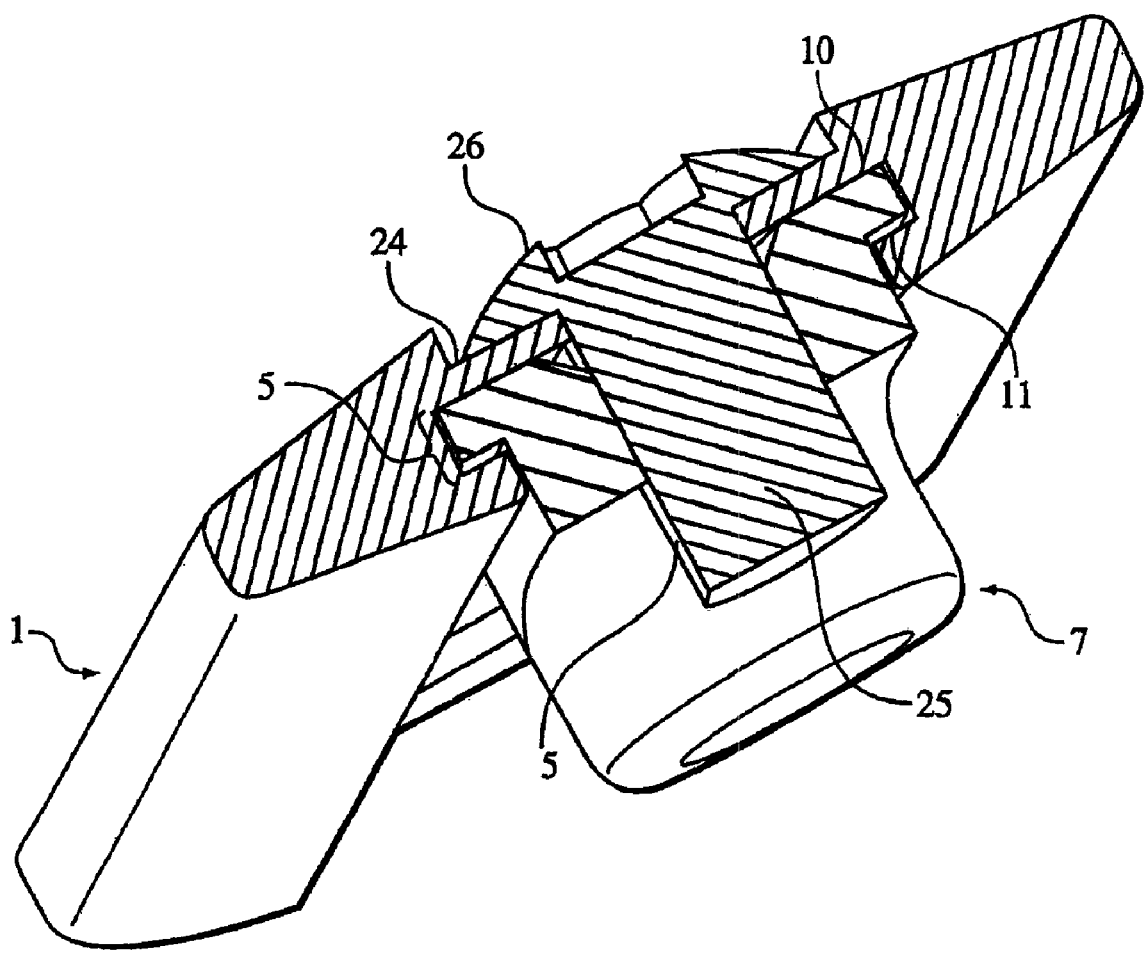
FIG. 4C is a drawing showing a screw, locker aperture and cavity means for locking the anchor assembly to the support element.

As shown in FIGS. 4A-4C, the anchor assembly 7 includes a means for locking the anchor assembly 7 to the support element 1. In one implementation, as shown in FIG. 4A, where the receiver 5 and complimentary anchor assembly 7 are T-slot shaped, the means for locking the anchor assembly 7 can be a setscrew 17 disposed within a threaded anchor assembly 7 locker aperture 15; wherein turning the setscrew 17 causes the setscrew 17 to move up toward the top portion 2 of the support element 1, where the setscrew 17 engages the receiver 5 planar upper face 10. When the setscrew 17 engages the receiver 5, the anchor assembly 7 presses against the receiver 5 planar lower face 11 to effect locking (See FIGS. 2C and 4A). Alternatively, a cam can be substituted for the setscrew 17 to effect the locking of the anchor assembly 7 within the support element 1.

In a further implementation, as shown in FIG. 4B, where the receiver 5 and complimentary anchor assembly 7 are T-slot shaped, the means for locking the anchor assembly 7 includes a threaded blind aperture 18 having a tapered slot 19 substantially aligned with the receiver 5 path. The threaded blind aperture 18 terminates in a floor 20 with a channel 21 cut therethrough. The threaded blind aperture 18 and a setscrew 17 are sized such that when engaged (i.e., screwed downward), the setscrew 17 causes expansion of the anchor assembly 7 walls 22 outwardly, whereupon contact is made between the anchor assembly 7 walls 22 and the receiver 5 medial surface to effect locking. Alternatively, a cam can be substituted for the setscrew 17 to effect the locking of the anchor assembly 7 within the support element 1.

In another implementation, as shown in FIG. 4C, where the receiver and complimentary anchor assembly 7 are T-slot shaped, the means for locking the anchor assembly 7 includes a locker aperture 15 having a screw 25, cam or the likes which can be lockably connected to the anchor assembly 7. Additionally, in this implementation the top portion 2 of support element 1 includes a cavity 24 or recess, substantially aligned with the receiver 5 for accommodating a screw head 26 or cam. In use, when the screw head 26 of the screw 25 engages the cavity 24 of the receiver 5, the anchor assembly 7 is drawn against the receiver 5 planar upper face 10 to effect locking (See FIGS. 2C and 4C). Alternatively, a cam can be substituted for the screw 25 to effect the locking of the anchor assembly 7 within the support element 1. In another implementation, the screw head 26 is configured as a button head style (see FIG. 4C) providing a low profile within the cavity 24 such that the screw head 26, can be positioned within the support element 1 without protruding above the top portion 2.

In other implementations where the receiver 5 and complimentary anchor assembly 7 are of alternative shapes or configurations (e.g. dove tail or rounded), an analogous means of locking is provided.

As shown in FIG. 3C, the anchor assembly 7 includes a base 9 moveably disposed within the threaded base aperture 16. The base 9 can be a screw, staple, hook or nail and of a type typically used for anchoring to a structure (e.g., a bone). In one implementation, the base 9 is screw of a type for insertion into the pedicle of a vertebrae. In another implementation, the base can be attached to another bony structure.

Attachment of the base 9 to the anchor assembly 7 can be made in any of a number of ways. In one implementation, the attachment is through a hinge-type of connection between the base 9 and the anchor assembly 7. In another implementation, as shown in FIG. 3C, the attachment is made between a polyaxial-type base head 8 on the base 9 and a complimentary receptacle 23 within the anchor assembly 7.

The anchor assembly 7 further includes a means for locking the base 9 within the anchor assembly 7. As shown in FIG. 3C, for a polyaxial-type base head 8, the means for locking can include a setscrew 17 disposed within the threaded base aperture 16. In this configuration, turning the setscrew 17 causes the setscrew 17 to press directly against the polyaxial head, thereby forcing the polyaxial head against the receptacle 23 of the anchor assembly 7 to effect locking. Alternatively, where the base 9 is of the hinge-type, the means for locking could be comprised of a setscrew 17 disposed in a threaded base aperture 16. In this configuration, turning the setscrew 17 causes the setscrew 17 to press directly against the base head 8 of the hinge-type base 9, thereby creating friction against the hinge's pin to effect locking (not shown). In another implementation, a cam can be substituted for the setscrew 17 to effect locking.

Support element 1 and a one or more anchor assemblies 7, once assembled, can be used to support a bony structure. When mated, the support element 1 and one or more anchor assemblies 7 form a support assembly. The bony structure supported can include a femur or other bones of the leg (e.g. tibia and fibula), bones of the arm and wrist (e.g. humerus, radius and ulna), calcaneous, pelvis, spine and the like. Support can be provided for a single bone (i.e. a long bone such as the femur, tibia, humerus) or for more than one bone (i.e. vertebrae).

In use, the support assembly can support a bony structure wherein the support element 1 is disposed within a body location including the subcutaneous fat layer of the back, muscle, cartilage, bone and the like. Alternatively, the support element 1 is disposed adjacent to bone. In another implementation, the support element 1 is disposed external to the body.

Additionally, the support assembly includes a freedom of movement with regard to the base 9 within the anchor assembly 7 and the anchor assembly 7 within the support element 1. That is, prior to locking respective base 9 and the anchor assembly 7 elements of the support assembly (hereinafter referred to as an unlocked configuration), the elements of the support assembly are movable and have one or more degrees of freedom so as allow for movement of the underlying structure being supported. For example, in the unlocked configuration, the support assembly is configurable so as to facilitate manipulation of vertebral disk spacing and spine curvature. Since the base 9 and anchor assembly 7 can be tightened and loosened by independent locking means, an option is provided to increase or decrease the vertebral disk space/height, or to increase or decrease the amount or lordotic/kyphotic curve of the spine, also called curvatures of the spine.

A method of use of the invention for effecting a desired vertebral disk spacing, can include the steps of: 1) implanting the bases 9 of a plurality of anchor assemblies 7 into vertebrae, wherein the bases 9 of the anchor assemblies 7 are unlocked for free movement; 2) interconnecting the anchor assemblies 7 with the receiver 5 of the support element 1, wherein the anchor assemblies 7 are unlocked within the receiver 5; 3) locking the bases 9 within the anchor assemblies 7 using a setscrew 17 or cam; 4) compressing or distracting the bases 9 in relation to each other to achieve a parallel displacement of the instrumented vertebrae; and 5) locking the anchor assemblies 7 within the support element 1 using a set screw 17 or cam.

"Instrumented" meaning where a physical connection exists between a structure (e.g. a vertebrae) and a medical device or instrument.

A method of use of the invention for effecting a desired curvature of the spine can include the steps of: 1) implanting the bases 9 of a plurality of anchor assemblies 7 into vertebrae, wherein the bases 9 of the anchor assemblies 7 are unlocked for free movement; 2) interconnecting the anchor assemblies 7 with the receiver 5 of the support element 1, wherein the anchor assemblies 7 are unlocked within the receiver 5; 3) compressing or distracting the bases 9 in relation to each other to affect the lordotic/kyphotic curvature of the spine; 4) locking the bases 9 within the anchor assemblies 7 and locking the anchor assemblies 7 within the support element 1, using a setscrew 17 or cam.

Another method of using the invention to support the spine can include the steps of: 1) setting a series of anchor assemblies 7 percutaneously in place along the spine through a series of small incisions including screwing a bone anchorage screw of each anchor assembly 7 into one or more adjacent pedicle portions of adjacent vertebrae in the spine, such that the anchor assemblies' receiver 5 mating parts align in a parallel plane within the subcutaneous fat layer of the back; 2) loading the support element 1 on top of the anchor assemblies including engaging the mated parts of the receiver 5 and the anchor assembly 7, either by sliding, snapping or otherwise positioning the support element 1 into the desired position; 3) accessing and locking the anchor assembly 7 in the support element 1 using the locking means feature of the anchor assembly 7 via the support element 1 apertures 6; and 4) optionally locking the bone anchorage screw feature of the anchor assembly 7 using the locking means feature for the bone anchorage screw via the support element 1 apertures 6.

The method of supporting the spine can also be used in conjunction with a kyphoplasty procedure. Kyphoplasty is a percutaneous technique involving the use of an expandable structure, such as a balloon catheter, to create a cavity or void within the vertebral body, followed by filling the cavity with a bone substitute to form an "internal cast". Methods and instruments suitable for such treatment are more fully described in U.S. Pat. Nos. 4,969,888 and 5,108,404, which are incorporated herein by reference. Kyphoplasty can be used to reduce vertebral compression fractures and to move bone with precision, thus restoring as close to normal the natural alignment of the vertebral column. Reduction of traumatic vertebral compression fractures have historically been treated with open reduction, internal fixation stabilization hardware and fusion techniques using a posterior approach. The usual role of stabilization hardware is to stop motion across the disk so that bone graft can fuse one vertebral body to the next. Usually, the stabilization hardware is left in permanently. In trauma repair, stabilization hardware is used to offload the fractured vertebral body so that the natural healing process can occur. In trauma, the stabilization hardware is designed to facilitate easy removal. Stabilization hardware can take many forms, including those described herein.

The combination of kyphoplasty and insertion of stabilization hardware utilizing the naturally occurring interior muscle plane as described in Wiltse and Spencer, Spine (1988) 13(6):696-706, satisfies the goals of improving the quality of patient care through minimally invasive surgical therapy.

A number of preferred embodiments of the invention have been described. Nevertheless, it will be understood that various modifications may be made without departing from the spirit and scope of the invention. For example, while the some implementations have been described using screws to anchor into bony structures, the scope of the invention is not so limited. Any means of anchoring can be used, such as a cam, screw, staple, nail, pin, or hook. Accordingly, other embodiments are within the scope of the following claims.

What is claimed is:

1. An implantable medical device for supporting bone comprising:
    a support element having:
        a top portion, and
        a bottom portion having a bottom surface and one or more apertures passing therethrough, the bottom surface of the support element including a receiver configured to receive a plurality of anchor assemblies; and
    the plurality of anchor assemblies, wherein each of the anchor assemblies includes:
        a means for locking the anchor assembly to the bottom portion of the support element, wherein the means for locking includes a locking aperture such that when the medical device is assembled, the means for locking the anchor assembly and the plurality of anchor assemblies do not pass through the support element,
    wherein the plurality of anchor assemblies are configured to be implanted into bone, and further comprising a base and a base head where the base head is configured to lock the base head to the base using a threaded base aperture and a setscrew; wherein turning the setscrew into the threaded base aperture results in engagement of the base head to effect locking.

2. The implantable medical device of claim 1, wherein the bone supported is selected from the group consisting of a spine, femur, tibia, fibula, humerus, radius, ulna, calcaneous, and a pelvis.

3. The implantable medical device of claim 1, wherein the base head is movably disposed within the anchor assembly.

4. The implantable medical device of claim 3, wherein the base head is selected from the group consisting of a polyaxial and a hinge-type connector.

5. The implantable medical device of claim 3, wherein the base is comprised of a means for locking the base in a desired position.

6. The implantable medical device of claim 1, wherein the one or more apertures have a dimensional configuration providing access to the base and the means for locking the base to the anchor assembly through the top portion of the support element.

7. The implantable medical device of claim 1, wherein the support element is elongate and sized to substantially span two or more vertebrae.

8. The implantable medical device of claim 1, wherein the support element has a shape selected from the group consisting of a board, plate, elongated cross-section, oval, square, I-beam and a rod.

9. The implantable medical device of claim 1, wherein the receiver is integrally disposed within the bottom surface of the bottom portion of the support element.

10. The implantable medical device of claim 1, wherein the receiver is attached to the bottom surface of the bottom portion of the support element.

11. The implantable medical device of claim 1, wherein the receiver has configuration selected from the group consisting of a slot, groove, track, dove tail and a one-way snap-in configuration.

12. The implantable medical device of claim 1, wherein the receiver has a 90-degree twist-in configuration such that the anchor assemblies are locked when the base is rotated in the 90-degree twist-in configuration.

13. The implantable medical device of claim 1, wherein the receiver and the anchor assembly are configured in an interconnecting geometry comprising a T-slot.

14. The implantable medical device of claim 13, wherein the T-slot configuration of the receiver comprises a planar upper face, a planar lower face and a planar medial face.

15. The implantable medical device of claim 1, wherein the receiver substantially spans the length of the bottom surface.

16. The implantable medical device of claim 1, wherein the receiver is comprised of a plurality of ends.

17. The implantable medical device of claim 16, wherein a first end of the receiver is open and a second end is closed.

18. The implantable medical device of claim 16, wherein a first and second end of the receiver are both open.

19. The implantable medical device of claim 16, wherein first and second ends of the receiver are both closed.

20. The implantable medical device of claim 1, wherein the receiver is comprised of a plurality of access ports sized for coupling the anchor assembly to the receiver distally from the receiver ends.

21. The implantable medical device of claim 1, wherein the receiver is configured to receive the anchor assemblies in two dimensions.

22. The implantable medical device of claim 1, wherein the anchor assembly has a configuration selected from the group consisting of a slot, groove, track, dove tail and a one-way snap-in configuration.

23. The implantable medical device of claim 1, wherein the anchor assembly has a 90-degree twist-in configuration.

24. The implantable medical device of claim 1, wherein the anchor assembly has a T-slot configuration.

25. The implantable medical device of claim 1, wherein the base is selected from the group consisting of a screw, staple, nail, hook and a pin.

26. The implantable medical device of claim 25, wherein the screw is a bone screw.

27. The implantable medical device of claim 26, wherein the bone screw is a pedicle screw.

28. An implantable medical device for supporting bone comprising:
   a support element having:
      a top portion, and
      a bottom portion having a bottom surface and one or more apertures passing therethrough, the bottom surface of the support element including a receiver configured to receive a plurality of anchor assemblies; and
   the plurality of anchor assemblies, wherein each of the anchor assemblies includes:
      a means for locking the anchor assembly to the bottom portion of the support element, wherein the means for locking includes a locking aperture such that when the medical device is assembled, the means for locking the anchor assembly and the plurality of anchor assemblies do not pass through the support element,
   wherein the plurality of anchor assemblies are configured to be implanted into bone, wherein the receiver and the anchor assembly are configured in an interconnecting geometry comprising a T-slot and the T-slot configuration of the receiver comprises a planar upper face, a planar lower face and a planar medial face, wherein the means for locking the anchor assembly to the support element includes
   a setscrew disposed within the locking aperture;
   wherein the setscrew and locking aperture are threaded so as to lockably engage the receiver planar upper face upon turning; and
   wherein upon so engaging the receiver planar upper face, the setscrew causes the anchor assembly to press against the receiver lower planar face to effect locking.

29. An implantable medical device for supporting bone comprising:
   a support element having:
      a top portion, and
      a bottom portion having a bottom surface and one or more apertures passing therethrough, the bottom surface of the support element including a receiver configured to receive a plurality of anchor assemblies; and
   the plurality of anchor assemblies, wherein each of the anchor assemblies includes:
      a means for locking the anchor assembly to the bottom portion of the support element, wherein the means for locking includes a locking aperture such that when the medical device is assembled, the means for locking the anchor assembly and the plurality of anchor assemblies do not pass through the support element,
   wherein the plurality of anchor assemblies are configured to be implanted into bone, wherein the receiver and the anchor assembly are configured in an interconnecting geometry comprising a T-slot and the T-slot configuration of the receiver comprises a planar upper face, a planar lower face and a planar medial face, wherein the means for locking the anchor assembly to the support element includes
   a cam disposed within the locking aperture;
   wherein the cam is disposed so as to lockably engage the receiver planar upper face upon turning; and
   wherein upon so engaging the receiver planar upper face, the cam causes the anchor assembly to press against the receiver lower planar face to effect locking.

30. An implantable medical device for supporting bone comprising:
   a support element having:
      a top portion, and
      a bottom portion having a bottom surface and one or more apertures passing therethrough, the bottom surface of the support element including a receiver configured to receive a plurality of anchor assemblies; and
   the plurality of anchor assemblies, wherein each of the anchor assemblies includes:
      a means for locking the anchor assembly to the bottom portion of the support element, wherein the means for locking includes a locking aperture such that when the medical device is assembled, the means for locking the anchor assembly and the plurality of anchor assemblies do not pass through the support element,
   wherein the plurality of anchor assemblies are configured to be implanted into bone, wherein the receiver and the anchor assembly are configured in an interconnecting geometry comprising a T-slot and the T-slot configuration of the receiver comprises a planar upper face, a planar lower face and a planar medial face, wherein the means for locking the anchor assembly to the support element is comprised of a threaded blind aperture having a slot substantially aligned longitudinally with the receiver thereby providing expandable walls, a floor having a cut channel therethrough and a setscrew; and
   wherein turning the setscrew into the blind aperture causes the walls to expand outwardly;
   wherein the walls engage the receiver planar medial surface to effect locking.

31. An implantable medical device for supporting bone comprising:
   a support element having:
      a top portion, and
      a bottom portion having a bottom surface and one or more apertures passing therethrough, the bottom surface of the support element including a receiver configured to receive a plurality of anchor assemblies; and
   the plurality of anchor assemblies, wherein each of the anchor assemblies includes:
      a means for locking the anchor assembly to the bottom portion of the support element, wherein the means for locking includes a locking aperture such that when the medical device is assembled, the plurality of anchor assemblies do not pass through the support element; and
      a base and a base head where the base head is configured to lock the base head to the base using a cam;
      wherein the cam is disposed such that turning the cam results in engagement of the base head with the cam to effect locking, wherein the plurality of anchor assemblies are configured to be implanted into bone.

32. A method for effecting a desired curvature of the spine comprising:
   1) implanting a plurality of anchor assemblies having bases and a first and second locking means into vertebrae of the spine, wherein the bases of the anchor assemblies are unlocked for free movement;

2) interconnecting each of the plurality of anchor assemblies within a receiver of a support element, wherein the anchor assemblies are unlocked within the receiver;
3) compressing or distracting the bases of one or more of the plurality of anchor assemblies in relation to each other to affect the vertebrae of the spine;
4) locking the bases within the anchor assemblies using the first locking means; and
5) locking the anchor assemblies within the support element using the second locking means, where the plurality of anchor assemblies and second locking means do not pass through the support element when the plurality of anchor assemblies are locked within the support element by the second locking means.

33. The method of claim 32, wherein:
the receiver and the anchor assemblies are configured in an interconnecting geometry comprising a T-slot and the T-slot in the receiver comprises a planar upper face, a planar lower face and a planar medial face and the second locking means includes a locking aperture and a setscrew disposed within the locking aperture; and
locking the anchor assemblies within the support element includes threading the setscrew in the locking aperture to lockably engage the receiver planar upper face and upon so engaging the receiver planar upper face, the setscrew causes the anchor assembly to press against the receiver lower planar face to effect locking.

34. The method of claim 32, wherein:
the receiver and the anchor assemblies are configured in an interconnecting geometry comprising a T-slot and the T-slot in the receiver comprises a planar upper face, a planar lower face and a planar medial face and the second locking means includes a locking aperture and a cam disposed within the locking aperture; and
locking the anchor assemblies within the support element includes turning the cam to lockably engage the receiver planar upper face and upon so engaging the receiver planar upper face, the cam causes the anchor assembly to press against the receiver lower planar face to effect locking.

35. The method of claim 32, wherein:
the receiver and the anchor assemblies are configured in an interconnecting geometry comprising a T-slot and the T-slot in the receiver comprises a planar upper face, a planar lower face and a planar medial face and the second locking means is comprised of a threaded blind aperture having a slot substantially aligned longitudinally with the receiver thereby providing expandable walls, a floor having a cut channel therethrough and a setscrew; and
locking the anchor assemblies within the support element includes turning the setscrew into the blind aperture to outwardly expand the expandable walls and engage the expandable walls to the receiver planar medial surface to effect locking.

36. The method of claim 32, wherein:
the second locking means further comprises a base and a base head where the base head is configured to lock the base head to the base using a cam; and
locking the anchor assemblies within the support element includes turning the cam to engage the base head with the cam and effect locking.

37. The method of claim 32, wherein compressing or distracting the bases of one or more of the plurality of anchor assemblies in relation to each other affects the lordotic or kyphotic curvature of the vertebrae.

38. The method of claim 32, wherein compressing or distracting the bases of one or more of the plurality of anchor assemblies in relation to each other affects the displacement of the vertebrae.

* * * * *